US006312904B1

(12) United States Patent
Schmidt et al.

(10) Patent No.: US 6,312,904 B1
(45) Date of Patent: Nov. 6, 2001

(54) CHARACTERIZING NUCLEIC ACID

(75) Inventors: Günter Schmidt, Houghton; Andrew Hugin Thompson, Alloway, both of (GB)

(73) Assignee: Xzillion GmbH & Co. KG, Frankfurt (DE)

( * ) Notice: Subject to any disclaimer, the term of this patent is extended or adjusted under 35 U.S.C. 154(b) by 0 days.

(21) Appl. No.: 09/462,600

(22) PCT Filed: Jul. 13, 1998

(86) PCT No.: PCT/GB98/02044

§ 371 Date: Apr. 10, 2000

§ 102(e) Date: Apr. 10, 2000

(87) PCT Pub. No.: WO99/02726

PCT Pub. Date: Jan. 21, 1999

(30) Foreign Application Priority Data

Jul. 11, 1997 (GB) ................................................... 9714717
Sep. 10, 1997 (GB) ................................................... 9719284
Dec. 19, 1997 (GB) ................................................... 9726949

(51) Int. Cl.[7] .............................. C12Q 1/68; C12P 19/34
(52) U.S. Cl. ............................................ 435/6; 435/91.1
(58) Field of Search ................................... 435/6; 536/27

(56) References Cited

U.S. PATENT DOCUMENTS

| 5,003,059 | * | 3/1991 | Brennan | 536/27 |
| 5,508,169 | * | 4/1996 | Deugau et al. | 435/6 |
| 5,547,835 | * | 8/1996 | Koster | 435/6 |

FOREIGN PATENT DOCUMENTS

| 40 11 991 | 10/1990 | (DE) . |
| WO 94/01582 | 1/1994 | (WO) . |
| WO 95/04160 | 2/1995 | (WO) . |
| WO 98/15652 | 4/1998 | (WO) . |

OTHER PUBLICATIONS

Fu et al., Nucleic Acids Research, vol. 25, No. 3, 1997, pp. 677–679, XP000196977.
Guilfoyle et al., Nucleic Acids Research, vol. 9, No. 25, pp. 1854, XP002076198.
Koster et al., Nature Biotechnology, vol. 14, Sep. 1996, pp. 1123–1128, XP002081617.

* cited by examiner

Primary Examiner—Kenneth R. Horlick
Assistant Examiner—Teresa Strzelecka
(74) Attorney, Agent, or Firm—Burns, Doane, Swecker & Mathis, L.L.P.

(57) ABSTRACT

The present invention involves a method for characterizing nucleic acid which comprises generating Sanger ladder nucleic acid fragments from a plurality of nucleic acid templates present in the same reaction zone, wherein at least one terminating base is present in the reaction zone. Prior to generating nucleic acid fragments, a labeled primer nucleotide or oligonucleotide is hybridized to each template. The label on each primer is specific to the template to which that primer hybridizes, thereby allowing for identification of the template. The method of the present invention further comprises identifying the length of each nucleic acid fragment produced, the template from which the fragment is derived and the terminating base of the fragment.

21 Claims, No Drawings

CHARACTERIZING NUCLEIC ACID

This invention relates to methods of nucleic acid sequencing. More specifically this application relates to high throughput methods of generating Sanger sequence termination ladders of multiple templates and methods of operating and analysing those ladders simultaneously.

Most nucleic acids of interest are large molecules which may be from a few kilobases to hundreds of megabases in length. Since current sequencing technologies only permit routine sequencing of fragments of about 500 to 600 bases in a single run, it is not possible to sequence such large molecules directly. A major cost in any large scale sequencing project is fragmenting large DNA molecules and isolating each sub-fragment to allow it to be amplified and sequenced. This sequence information must then be collated and analysed to determine the sequence of the source molecule. This is usually done by molecular cloning methods.

Cloning for sequencing is typically performed as follows. A large DNA molecule is fragmented, generally with a type II restriction endonuclease, to generate a 'library' of DNA fragments. These DNA fragments are then ligated into vectors that can be cultured in a biological host. Isolation of individual DNA molecules from the library is effected by limiting dilution of the culture of the host organism such that subsequent plating out of the medium onto agar culture dishes results in the growth of colonies of the host derived from a single organism bearing only one of the DNA fragments from the library.

Various strategies for high throughput sequencing have been developed which exploit the methods of molecular cloning. Typically a hierarchy of cloning is performed. Very large DNA molecules such as human chromosomes are typically cleaved using restriction endonucleases which cut rarely thus generating large fragments. These are cloned into vectors which can accommodate such large fragments which are then transfected into an appropriate host. Yeast Artificial Chromosomes (YACs) are often used for this purpose. These are transfected into *S. cerevisiae*. The vector sequences flanking a clone are known and these can be used to 'end sequence' a large clone, identifying short sequences that identify the termini of the clone. These can be used to generate oligonucleotide probes. These probes are used to screen libraries of clones. Overlapping clones may be identified by hybridising an oligonucleotide probe to blots of isolated colonies of the host organism. Pairs of probes from different clones which hybridise to a third clone, generally indicate that the third clone spans the gap between the clones providing the probes. A series of clones can thus be ordered identifying their positions in the genome. This identifies gaps and thus missing clones which can be subsequently isolated. Once an ordered library of clones has been generated, these clones can then be sequenced by sub-cloning the large clones into vectors which carry shorter fragments such as Bacterial Artificial Chromosomes or M13 phages. These sub-clones may be ordered by end-sequencing again or may be sequenced directly in their entirety.

A typical approach to the sequencing a library of clones derived from a large source molecule starts with a 'shotgun sequencing' phase followed by a directed 'finishing' phase. Shotgun sequencing uses random selection of the clones to be sequenced. The initial selections of a shotgun sequencing project generate a lot of unique clones but as the proportion of a library that has been sequenced increases, more and more clones are re-sequenced by random selection. This means that a considerable amount of redundant sequencing is done if one wishes to completely sequence a library by shotgun approaches. For this reason it is usual to perform an initial shotgun phase to sequence a pre-determined proportion of a library. Once this is done, contiguous sequences are identified from the sequences that have been determined. Once these 'contigs' have been identified, the sequences that flank the contigs can be used to identify and sequence clones that span the gaps between contigs. This finishing phase is expensive and relatively slow.

It would be desirable for the purpose of large scale sequencing projects to be able to automate the procedures required in the sequencing process. Unfortunately the processes currently used that are based on molecular cloning are amenable to partial automation using equipment that requires skilled operators. Furthermore the methods are slow. In order to reduce the costs of sequencing the genomes of organisms of commercial and scientific value, it would be beneficial to develop methods that fully automate the fragmentation and ordering of clones and to further automate the process of sub-cloning and sequencing of ordered clones.

Sequencing

Conventional DNA sequencing according to the Sanger methodology uses a DNA polymerase to add numerous dideoxy/deoxynucleotides to an oligonucleotide primer, annealed to a single stranded DNA template, in a template specific manner. Random termination of this process is achieved when terminating nucleotides, i.e. the dideoxynucleotides, are incorporated into the template complement. A 'DNA ladder' is produced when the randomly terminated strands are separated on a denaturing polyacrylamide gel. Sequence information is gathered, using polyacrylamide gel electrophoresis to separate the terminated fragments by length, followed by detecting the 'DNA ladder' either through incorporating a radioactive isotope or fluorescent label into one of the terminating nucleotides or the primer used in the reaction. The main draw back with this technology is its dependence on conventional gel electrophoresis, to separate the DNA fragments in order to deduce sequence information, as this is a slow process taking up to nine hours to complete.

The separation of a Sanger Ladder by gel electrophoresis imposes limitations on the throughput and accuracy achievable for DNA sequencing. The polymerase reaction used to generate a Sanger ladder is simple and relatively fast and can readily be performed in parallel or even multiplexed in the same reaction. Various novel sequencing methods have been developed that are compatible with PCR and hence exploit automation using 96 well plate robotics and thermocyclers.

Gel electrophoresis works on the simple principle that a charged molecule placed between two electrodes will migrate towards the electrode with the opposite charge to its own. The larger the molecule is for a given charge the more slowly it will migrate towards the relevant electrode. Nucleic acids are poly-ions, carrying approximately one charge per nucleotide in the molecule. This means that nucleic acids of any size migrate at approximately the same rate ignoring frictional forces from the separation medium. The effect of frictional forces is related to the size of the molecule or in the case of nucleic acids, the length of the molecule. This means that nucleic acids are effectively separated by length. The role of the gel matrix is to provide frictional force to impede migration. The speed of separation is proportional to the size of the electric field between the two electrodes. This means that increasing the size of the electric field will reduce separation times, however the electrical resistance of the separation medium means that heat is generated as a result of the electric field and the heat increases with the electric field. The higher temperatures increase the kinetic energy imparted to the analyte leading to greater diffusion and band broadening. This reduces the resolution of the separation. Gels can be cooled but heat dissipation from a slab gel is limited by its surface/volume ratio which is essentially a function of the thickness of the gel. Thinner gels dissipate heat better but there is an additional effect of increased resistance. This means that in slab gel techniques using gels of 200 to 400 μm thickness heating becomes severe if the electric field strength is greater than 50 V/cm. Replacement of the slab gel electrophoretic steps is the most attractive target in view to increasing the overall speed of DNA sequencing. Capillary electrophoresis offers significant advantages over gel electrophoresis as a separation technology. Various approaches to capillary electrophoresis exist but for nucleic acid separations capillary gel electrophoresis is often used. This technique is essentially gel electrophoresis in a narrow tube. The use of a capillary gives an improved surface/volume ratio which results in much better thermal dissipation properties. This allows much higher electric fields to be used to separate nucleic acids greatly increasing the speed of separations. Typically capillaries are 50 to 75 μm wide, 24 to 100 cm long and electric fields up to 400 v/cm can be used although lower fields are used routinely. Increased separation speeds also improve the resolution of the separation as there is less time for diffusion effects to take place and so there is less band broadening. Improved resolution permits greater read lengths, increasing throughput further. The introduction of flowable polymers has meant that time consuming and technically demanding steps of gel preparation associated with slab gel electrophoresis can be avoided and capillaries can be prepared by injection of the sieving matrix. This improves the reproducibility of separations and the injection of polymers is a process which is readily automated.

The detection of nucleic acids after separation is typically achieved using fluorescent labels which are incorporated into the nucleic acid during its preparation. Automated capillary electrophoresis systems coupled to fluorescent detection are commercially available (e.g. the ABI310 from Perkin Elmer Applied Biosystems). However fluorescent labelling schemes permit the labelling of a relatively small number of molecules simultaneously, typically 4 labels can be used simultaneously and possibly up to eight. However the costs of the detection apparatus and the difficulties of analysing the resultant signals limit the number of labels that can be used simultaneously in a fluorescence detection scheme. Furthermore the very small volumes of analyte used in capillary electrophoresis make detection by fluorescence very demanding.

An advantage of mass labelling is the possibility of setting aside a number of labels to be attached to size standards which can be included in every assay. This will then allow the migration of different templates to be relaxed to that of fragments of known length. This will facilitate comparison of data from different analyses. This is particularly useful in assays analysing genetic markers such as micro-satellites.

Mass spectrometry offers significant advantages over fluorescence as a detection scheme. Mass spectrometry can routinely detect very small amounts of analyte in very small volumes of solvent.

U.S. patent application Ser. No. 09/341,646, filed Sep. 20, 1999, describes arrays of cleavable labels that are detectable by mass spectrometry which identify the sequence of a covalently linked nucleic acid probe. These mass labels have a number of advantages over other methods of analyzing nucleic acids. At present commercially favored systems are based on fluorescent labeling of DNA. Fluorescent labeling schemes permit the labeling of a relatively small number of molecules simultaneously, typically 4 labels can be used simultaneously and possibly up to eight. However the costs of the detection apparatus and the difficulties of analyzing the resultant signals limit the number of labels that can be used simultaneously in a fluorescence detection scheme. An advantage of using mass labels is the possibility of generating large numbers of labels (several hundred) which have discrete peaks in a mass spectrum allowing similar numbers of distinct molecular species to be labeled simultaneously. Fluorescent dyes are expensive to synthesize whereas mass labels can comprise relatively simple polymers permitting combinatorial synthesis of large numbers of labels at relatively low cost. U.S. application Ser. No. 09/341,646, filed Sep. 20, 1999 discloses further mass labels and cleavable linkers which can be used in the present invention.

U.S. patent application Ser. No. 09/462,408, filed Apr. 10, 2000, describes sequencing by capillary electrophoresis mass spectrometry (CEMS) exploiting the mass labels of U.S. patent application Ser. No. 09/341,646, filed Sep. 20, 1999. Capillary electrophoresis (CE) is used to separate Sanger sequence ladders by length. The ladders are labeled with mass labels identifying the template and the terminating base. The separated fragments are introduced in-line from the CE column into an electrospray mass spectrometer where the labels are cleaved from the nucleic acid and are identified by their mass to charge ratio. The arrival of fragments from the CE column identifies the sequence of bases in each fragment. The advantage of CE separations over conventional gel electrophoresis is the reduced separation time, improved reproducibility of separations and automation of matrix loading and sample loading.

PCT/GB98/02789 describes sequencing by tandem mass spectrometry (TMS) exploiting the mass labels of U.S. patent application Ser. No. 09/462,408, filed on Apr. 10, 2000. With mass labeled Sanger ladders, terminated nucleic acid fragments are separated by length in the first mass analyzer, followed by cleavage of the label between mass analyzers, and finishing with identification of the mass labels in the second mass analysis stage. Separating ladders by length needs a mass resolution of approximately 300 Daltons wherein direct analysis requires a resolution of 4 to 5 Daltons. Thus it should be possible to analyze considerably longer sequencing fragments by Tandem mass spectrometry of mass labeled Sanger ladders.

It is an object of this invention to provide methods to increase the throughput of the sequencing of libraries of fragments using multiplexing techniques based on the mass labeling technology disclosed in U.S. patent application Ser. No. 09/341,646, filed Sep. 20, 1999, and the CEMS sequencing technology disclosed in U.S. patent application Ser. No. 09/462,408, filed Apr. 10, 2000, or the TMS sequencing techniques of PCT/GB98/02789. The methods of this invention can exploit simple liquid handling robotics or microfluidics and can dispense with the need for sub-cloning of large DNA fragments into sequencing vectors such as M13 phage. In conjunction with methods for automated isolated and identification of large nucleic acid fragments, it would be possible to fully automate the process of fragmentation and isolation of overlapping fragments using the methods of the prior art and this invention. In conjunction with automated sequencing techniques, it would be possible to fully automate the entire sequencing process.

Accordingly, the present invention provides a method for characterising nucleic acid, which method comprises generating Sanger ladder nucleic acid fragments from a plurality of nucleic acid templates present in the same reaction zone, at least one terminating base being present in the reaction zone, and for each nucleic acid fragment produced identifying the length of the fragment, the identity of the template from which the fragment is derived and the terminating base of the fragment, wherein prior to generating the fragments, a labelled primer nucleotide or oligonucleotide is hybridised to each template, the label on each primer being specific to the template to which that primer hybridises to allow identification of the template.

The labels used in the present invention are preferably mass labels. PCT/GB98/00127 and the UK patent applications of Page White and Farrer file numbers 87820, 87821 and 87900 disclose mass label and cleavable linkers which can be used in the present invention.

Multiplexing Sanger Ladder Detection

Conventional DNA sequencing according to the Sanger methodology uses a DNA polymerase to add numerous dideoxy/deoxynucleotides to an oligonucleotide primer, annealed to a single stranded DNA template, in a template specific manner. Random termination of this process is achieved when terminating nucleotides, i.e. the dideoxynucleotides, are incorporated into the template complement. A 'DNA ladder' is produced when the randomly terminated strands are separated on a denaturing polyacrylamide gel. Sequence information is gathered, following polyacrylamide gel electrophoresis, by detecting the 'DNA ladder' either through incorporating a radioactive isotope or fluorescent label into one of the nucleotides or the primer used in the reaction.

Given a large number of labels to resolve ladders generated from one template from ladders from other templates, one can multiplex the analysis of a series of Sanger sequencing reactions. One can analyze Sanger ladders derived from different templates simultaneously as long as each template is identified by a unique label. Preferably all four termination reactions are analyzed simultaneously which is possible if each template is identified by 4 labels where each terminating base is identified by a discrete label. The labels may be attached to the terminating base or it may be attached to the primer used in the sequencing reaction.

Multiplexed analysis of sequencing reactions according to the methods of this invention can be performed on Sanger ladders generated simultaneously in the same reaction. Alternatively multiplexed analysis can be performed on ladders generated from templates in spatially discrete reactions which are then pooled prior to analysis.

Sanger sequencing requires the presence of a primer to permit a polymerase to copy a single stranded nucleic acid. This requires knowledge of a short stretch of sequence in the template to allow a complementary oligonucleotide primer to be synthesised. If a cloning vector is used the sequence is provided by the vector sequence flanking the incorporated clone. It is a further object of this invention to provide arrays of primers for multiplexed sequencing reactions and to provide methods of introducing primer binding sites into sequencing templates.

Multiplexing with Generic Flanking Sequences

In outline, one aspect of the methods of this invention comprise the steps:
1. Generating a library of nucleic acids fragments with a stretch of known sequence 3' of a region of unknown sequence that is to be determined.
2. Contacting the library with a labelled primer or, if sufficient labels are available, uniquely labelled primers complementary to the known 3' sequence with an additional stretch of bases overlapping into the unknown sequence adjacent to the known sequence. The label on each primer identifies the overlap of each primer.
3. Adding polymerase, which is preferably thermostable, nucleotide triphopshate sufficient to permit complete replication of the template through extension of the annealed primers and a terminating nucleotide to generate fragments terminated randomly at the positions of the nucleotide in the template complementary to the terminating nucleotide.
4. Optionally, thermally denaturing the terminated fragments and allowing hybridization of the primer from step (2) to effect further copies of the terminated fragments to be generated in a cyclic reaction. This would require a thermostable polymerase in step (3).
5. Determining the length of each of the extended fragments, to identify its terminating base and determining the identity of each of the amplified fragments by detection of the label incorporated with its primer.

Multiplexing with Unique Flanking Sequences

In outline, a second aspect of the methods of this invention comprises the steps:
1. Generating a library of nucleic acids fragments such that each different nucleic acid has a stretch of known sequence 3' of a region of unknown sequence that is to be determined and the stretch of known sequence for each distinct fragment is also distinct from all others.
2. Contacting the library with a labelled primer or, if sufficient labels are available, uniquely labelled primers complementary to the known 3' sequences that identify each fragment in the library. The label on each primer identifies the sequence of each primer and hence the fragment to which it is complementary.
3. Adding polymerase, which is preferably thermostable, nucleotide triphosphates sufficient to permit complete replication of the template through extension of the annealed primers and a terminating nucleotide to generate fragments terminated randomly at the positions of the nucleotide in the template complementary to the terminating nucleotide.
4. Optionally, thermally denaturing the terminated fragments and allowing hybridization of the primer from step (2) to effect further copies of the terminated fragments to be generated in a cyclic reaction. This would require a thermostable polymerase in step (3).
5. Determining the length of each of the extended fragments, to identify its terminating base and determining the identity of each of the extended fragments by detection of the label incorporated with its primer.

Multiplexing Sequencing Reactions with Labelled Primers

Primer labelled sequencing permits the generation of multiple ladders simultaneously in the same reaction. Consider a library of templates where each template has a distinct known sequence at the 3' terminus. These sequences can be used to generate complementary primers for each template. Each primer can then be tagged with a unique label to identify the primer. The template mixture can be divided into four reactions in which only one of each of the four terminating dideoxynucleotides is present in each reaction. Each template is primed with its uniquely labelled primer. After performing each of the four Sanger reactions, each ladder can be resolved by length with subsequent identification of the labels on the sequence fragments.

For each template with a unique primer sequence, each unique primer can be identified with a different label in each of the four reactions to identify which terminating nucleotide is present. This would allow one to pool the four individual base sequencing reactions and analyse them simultaneously. This has the advantage that all four reactions are analysed under identical conditions which should avoid ambiguities that might arise when analysing the four reactions separately due to variations in conditions in each analysis.

One method of labeling that is appropriate is mass labeling with analysis of Sanger ladders by capillary electrophoresis mass spectrometry (U.S. patent application Ser. No. 09/462,208, filed Apr. 10, 2000). Each band that elutes from the capillary electrophoresis column that contains a terminated fragment can be related back to its source template by the label linked to its primer. In this way a large number of templates can be sequence simultaneously in the same reaction.

Primer Labelled Sequencing with Generic Primers

An embodiment of the first aspect of this invention comprises the steps of:

1. Optionally, contacting a large nucleic acid or population of large nucleic acids with a sequence specific cleavage agent to generate fragments. Preferably the sequence specific cleavage agent is a type II restriction endonuclease which generate fragments with known sticky ends.
2. Ligating adaptors or linkers to the terminal of these nucleic acid molecules. The ligated adaptor provides a known sequence at the termini of a population of nucleic acids which can be used to design primers which extend beyond the terminal adaptor sequence into unknown sequence adjacent to the known adaptor sequence allowing the unknown sequence to be probed.
3. Optionally amplifying the adaptored fragments using primers complementary to the whole or part of the adaptor sequences at the termini of the adaptored fragments.
4. Optionally normalising the population of adaptored nucleic acids.
5. Optionally selectively amplifying subsets of the nucleic acids according to the methods of U.S. Pat. No. 5,728,524.
6. Sub-dividing the population of nucleic acids into 4 separate reaction vessels.
7. For each of the 4 reaction vessels perform the following steps:
8. Optionally, capturing adaptored template nucleic acid libraries in each reaction vessel onto a solid phase support.
9. Denaturing the nucleic acid library to exposed single stranded nucleic acids. If the nucleic acid library was captured in step (8), denaturation will release the non-captured strand into solution which can be washed away, if desired, leaving a single-stranded nucleic acid on the solid phase support.
10. Contacting the single stranded templates, which may be on a solid support, with a labelled primer under conditions to permit hybridisation of the primer. The primer bears a sequence complementary to that provided by the adaptor and restriction site. The primer additionally bears an overlap of a predetermined number of bases beyond the known sequence into the unknown sequence immediately adjacent to the restriction site. The label on the primer identifies the sequence that overlaps beyond the known adaptor sequence into the unknown sequence of the template.
11. Adding polymerase, which is preferably thermostable, nucleotide triphosphates sufficient to permit complete replication of the template through extension of the annealed primers and a terminating nucleotide to generate fragments terminated randomly at the positions of the nucleotide in the template complementary to the terminating nucleotide.
12. Optionally, thermally denaturing the terminated fragments and allowing hybridization of the primer from step (10) to effect further copies of the terminated fragments to be generated in a cyclic reaction. This would require a thermostable polymerase in step (11).
13. Pooling the reaction products of the 4 separate reaction vessels.
14. Determining the length of each of the extended fragments, to identify its terminating base and determining the identity of each of the amplified fragments by detection of the label incorporated with its primer.

U.S. patent application Ser. No. 09/462,408, filed Apr. 10, 2000, and PCT/GB98/02789, describe nucleic acid probes labeled with markers that are resolvable by mass spectrometry. Such mass labeled probes would permit the analysis described here to be performed very rapidly as a captured library of restriction fragments can be probed with a number of uniquely mass labeled primers simultaneously.

Primer Labelled Sequencing with Unique Primers

U.S. Pat. No. 5,728,524 describes method of molecular sorting which exploit type IIS and IP restriction endonucleases. These enzymes generate ambiguous sticky-ends when they cleave a nucleic acid. Adapters are designed with sticky ends complementary to a single sticky-end sequence or a subset of these ambiguous sticky ends such that the individual sticky end or subset thereof is coupled to a distinct sequence in the double stranded region of the adapter. This allows subsets of the adaptored nucleic acid to be amplified using specific primers corresponding to sequences within the adapter which in turn relate to the sequence of the sticky end of the adapter.

U.S. Pat. No. 5,508,169 (issued Nov. 7, 1995) describes methods very similar to those disclosed in U.S. Pat. No. 5,728,524.

The methods disclosed in these applications permit unique primer sequences to be introduced to the termini of restriction fragments. These adaptored fragments are amenable to multiplexed sequencing using the methods of this invention.

Accordingly an embodiment of the second aspect of this invention comprises the steps of:

1. Optionally, contacting a large nucleic acid or population of large nucleic acids with a sequence specific cleavage agent to generate fragments. Preferably the sequence specific cleavage agent is a type IIS or IP restriction endonuclease to generate fragments with ambiguous sticky ends.
2. Contacting the fragment population of (1) with an array adaptors or linkers in the presence of a ligase. The array of adaptors comprises an end recognition capable of binding to the ambiguous termini of the restriction fragment population. The adaptors additionally comprise a sequence which is unique to each different end recognition means or subset thereof. The adaptors may additionally comprise a common sequence to permit amplification and sequences to facilitate ligation into cloning vectors.

3. Optionally amplifying the adaptored fragments using primers complementary to the whole or part of the adaptor sequences at the termini of the adaptored fragments.
4. Optionally normalising the population of adaptored nucleic acids.
5. Optionally selectively amplifying subsets of the nucleic acids according to the methods of U.S. Pat. No. 5,728,524.
6. Sub-dividing the population of nucleic acids into 4 separate reaction vessels.
7. For each of the 4 reaction vessels perform the following steps:
8. Optionally, capturing adaptored template nucleic acid libraries in each reaction vessel onto a solid phase support.
9. Denaturing the nucleic acid library to exposed single stranded nucleic acids. If the nucleic acid library was captured in step (8), denaturation will release the non-captured strand into solution which can be washed away, if desired, leaving a single-stranded nucleic acid on the solid phase support.
10. Contacting the single stranded templates, which may be on a solid support, with an array of labelled primers under conditions to permit hybridisation of the primers. The array comprises primers which each recognise at least one and preferably only one of the possible adaptor sequences present at the termini of the restriction fragment population. Each distinct primer bears a label that is uniquely identifiable. Preferably, the labels are resolved by mass spectrometry.
11. Adding polymerase, which is preferably thermostable, nucleotide triphosphates sufficient to permit complete replication of the template through extension of the annealed primers and a terminating nucleotide to generate fragments terminated randomly at the positions of the nucleotide in the template complementary to the terminating nucleotide.
12. Optionally, thermally denaturing the terminated fragments and allowing hybridization of the primer from step (10) to effect further copies of the terminated fragments to be generated in a cyclic reaction. This would require a thermostable polymerase in step (11).
13. Pooling the reaction products of the 4 separate reaction vessels.
14. Determining the length of each of the extended fragments, to identify its terminating base and determining the identity of each of the amplified fragments by detection of the label incorporated with its primer. The analysis is preferably performed using a CEMS or TMS system.

Multiplexing with Nucleotide Labelled Reactions

An alternative to the use of labelled primers to perform sequencing is to label the 4 terminating nucleotides. To permit multiplexed analysis, sets of 4 terminating nucleotides could be labelled with a different set of 4 labels in each reaction that is to be multiplexed. In the simplest scenario each template and its corresponding labels must spatially separated. Each sequencing reaction would be performed separately and then all the templates would be combined at the end of the sequencing reactions. The Sanger ladders generated are then all separated together in a CEMS sequencer or in a random mass spectrometer. Each set of 4 mass labels then correlates to a single source template.

The use of labelled nucleotides is a favourable embodiment in that it avoids certain potential problems associated with primer labelled sequencing. Polymerase reactions often terminate prematurely, without the intervention of blocked nucleotides. This is a problem with primer labelled sequencing because the premature termination generates a background of labelled fragments that are terminated incorrectly. Labelling the blocking nucleotides ensures only correctly terminated fragments are labelled so only these are detected in the analysis of labelled sequence ladders. Nucleotide labelling is often preferred if cycle sequencing is performed. In cycle sequencing, multiple rounds of primer extension are performed generating multiple copies of the sequence ladders. The sequencing reaction is performed using a thermostable polymerase. After each reaction the mixture is heat denatured and more primer is allowed to anneal with the template. The polymerase reaction is repeated when primer template complexes reform. Multiple repetition of this process gives a linear amplification of the signal, enhancing the reliability and quality of the sequence generated.

Consider a reaction in which unmodified ATP, CTP, GTP and TTP are present with the four corresponding uniquely mass labelled terminating nucleotides. Sanger sequence ladders can be generated for a number of templates simultaneously in the same reaction vessel. If these different templates share a sequencing primer, they can be subsequently sorted into separate groups prior to separation on the basis of the sequence immediately adjacent to the primer. The fragments could be sorted onto a hybridisation array where the array bears a sequence complementary to the sequencing primer at all points and an additional predetermined number of bases, N, such that each location on the array bears just one of the possible N base sequences. This means if N is 4 there would be 256 discrete locations on the array. It is expected that a group of templates would in most cases have distinct sequences immediately adjacent to the primer.

With a labelling system that provides a large number of labels, however, distinct sets of 4 labels can be used to identify blocking nucleotides in a large number of reactions. Thus multiple templates can be added to different reaction vessels, preferably different templates to each reaction vessel. After generating Sanger ladders in each vessel, the reactions can be pooled and the templates from each reaction can be sorted simultaneously. The majority of ladders of each template from each reaction would be expected to segregate to discrete locations on an array and that each location on the array would receive template ladders from a number of distinct reactions.

Having sorted ladders to discrete locations on an array, the ladders from each location must be recovered for analysis in which the length of each fragment of a ladder is determined and the mass label that terminates fragments of each length must be identified.

Practically speaking a hybridisation array could comprise an array of wells on microtitre plates, for example, such that each well contains a single immobilised oligonucleotide that is a member of the array. In this situation a sample of the pooled reactions is added to each well and allowed to hybridise to the immobilised oligonucleotide present in the well. After a predetermined time the unhybridised DNA is washed away. The hybridised DNA can then be melted off the capture oligonucleotide. The released DNA can then be loaded into a capillary electrophoresis mass spectrometer or it can be injected into the electrospray interface of a tandem mass spectrometer.

Equally, and preferably, the array could be synthesised combinatorially on a glass 'chip' according to the methodology of Southern or that of Affymetrix, Santa Clara, Calif.

(see for example: A. C. Pease et al. Proc. Natl. Acad. Sci. USA. 91, 5022–5026, 1994; U. Maskos and E. M. Southern, Nucleic Acids Research 21, 2269–2270, 1993; E. M. Southern et al, Nucleic Acids Research 22, 1368–1373, 1994) or using related ink-jet technologies such that discrete locations on the glass chip are derivitised with one member of the hybridisation array. One could hybridise the pooled sanger ladders to the chip and wash away unhybridised material. The chip can then be treated with a MALDI matrix material such as 3-hydroxypicolinic acid. Having prepared the chip in this way it can be loaded into a MALDI based tandem mass spectrometer and Sanger ladders from discrete locations on the array can be desorbed by application of laser light to the desired location on the array. Direct desorption of DNA from a hybridisation matrix has been demonstrated by Köster et al. (Nature Biotech. 14, 1123–1128). The length of the fragments can be analysed in the first mass analyzer followed by cleavage of labels and analysis of these labels in the second mass analyser.

Multiplexed Sequencing Using Generic Primers and Labelled Terminators

In outline, a further embodiment of the first aspect of this invention comprise the steps of:

1. Optionally, restricting a large nucleic acid or population of large nucleic acids to generate fragments with known termini.
2. Ligating adaptors or linkers to the termini of these nucleic acid molecules. The ligated adaptor provides a known sequence at the termini of a population of nucleic acids which can be used to design primers which extend beyond the terminal adaptor sequence into unknown sequence adjacent to the known adaptor sequence allowing the unknown sequence to be probed.
3. Optionally amplifying the adaptored fragments using primers complementary to the whole or part of the adaptor sequences at the termini of the adaptored fragments.
4. Optionally normalising the population of adaptored nucleic acids.
5. Optionally selectively amplifying subsets of the nucleic acids according to the methods of U.S. Pat. No. 5,728,524.
6. Capturing adaptored template nucleic acids onto a solid phase support.
7. Denaturing the captured nucleic acids to release the non-captured strand into solution which is washed away leaving a single-stranded nucleic acid on the solid phase support.
8. Contacting the single stranded templates on the solid support with a series of unlabeled primer under conditions to permit hybridization of the primer. The primer bears a sequence complementary to that provided by the adaptor and restriction site. The primer additionally bears an overlap of a predetermined number of bases beyond the known sequence into the unknown sequence immediately adjacent to the restriction site.
9. Adding thermostable polymerase, nucleotide triphosphate and 4 labeled terminating nucleotides to extend annealed primers and generate fragments terminated randomly at the positions of the nucleotide in the template complementary to the terminating nucleotide. Each terminating nucleotide carries a distinct label.
10. Optionally, thermally denaturing the terminated fragments and allowing hybridisation of the primer from step (8) to effect further copies of the terminated fragments to be generated in a cyclic reaction.
11. Sorting the template fragments onto a hybridization array bearing different oligonucleotides at distinct positions on the array. The array of oligonucleotides have sequences complementary to those used to prime the sequencing reactions in step (8).
12. Determining the length of each of the extended fragments and the identity of the label on the terminating base to identify the sequence of each template.

U.S. patent application Ser. No. 09/462,408, filed Apr. 10, 2000, and PCT/GB98/02789, describe nucleic acid probes labeled with markers that are resolvable by mass spectrometry. Such mass labeled probes would permit the analysis described here to be performed very rapidly as a captured library of restriction fragments can be probed with a number of uniquely mass labeled primers simultaneously.

Multiplexed Sequencing Using Unique Primers and Labelled Terminators

A further embodiment of the second aspect of this invention comprise the steps of:

1. Optionally, contacting a large nucleic acid or population of large nucleic acids with a sequence specific cleavage agent to generate fragments. Preferably the sequence specific cleavage agent is a type IIS or IP restriction endonuclease to generate fragments with ambiguous sticky ends.
2. Contacting the fragment population of (1) with an array adaptors or linkers in the presence of a ligase. The array of adaptors comprises an end recognition capable of binding to the ambiguous termini of the restriction fragment population. The adaptors additionally comprise a sequence which is unique to each different end recognition means or subset thereof. The adaptors may additionally comprise a common sequence to permit amplification and sequences to facilitate ligation into cloning vectors.
3. Optionally amplifying the adaptored fragments using primers complementary to the whole or part of the adaptor sequences at the termini of the adaptored fragments.
4. Optionally normalising the population of adaptored nucleic acids.
5. Optionally selectively amplifying subsets of the nucleic acids according to the methods of U.S. Pat. No. 5,728,524.
6. Capturing adaptored template nucleic acids onto a solid phase support.
7. Denaturing the captured nucleic acids to release the non-captured strand into solution which is washed away leaving a single-stranded nucleic acid on the solid phase support.
8. Contacting the single stranded templates, which may be on a solid support, with an array of labelled primers under conditions to permit hybridisation of the primers. The array comprises primers which each recognise at least one and preferably only one of the possible adaptor sequences present at the termini of the restriction fragment population.
9. Adding thermostable polymerase, nucleotide triphosphate and 4 labelled terminating nucleotides to extend annealed primers and generate fragments terminated randomly at the positions of the nucleotide in the template complementary to the terminating nucleotide. Each terminating nucleotide carries a distinct label.
10. Optionally, thermally denaturing the terminated fragments and allowing hybridisation of the primer from step (8) to effect further copies of the terminated fragments to be generated in a cyclic reaction.

11. Sorting the template fragments onto a hybridisation array bearing different oligonucleotides at distinct positions on the array. The array of oligonucleotides on the array comprise the sequences complementary to those used to prime the sequencing reactions in step (9) such that at each position on the array there is one primer complement.

12. Determining the length of each of the extended fragments and the identity of the label on the terminating base to identify the sequence of each template.

Preparation of Templates with Unique Primer Binding Sites

In order to perform multiplexed analysis of sequence ladders it is necessary that the Sanger ladder generated for each template be distinguishable from those generated from other templates. This can be achieved using uniquely labelled sequencing primers for each template.

In order to ensure that each template bears a unique sequencing primer site a family of cloning vectors could be engineered so that each member of the family bears a different primer sequence flanking the integration site for the exogenous DNA to be sequenced. Each sequencing reaction would be performed on a group of templates where only one template derived from each vector type is present so that all the templates in a reaction bear unique primers.

Brenner and Sorting Tags

Alternatively different primers can be linked to a 'sorting sequence', a length of oligonucleotide that could be used to sort ladders with different primers onto a hybridisation chip. Such sorting sequences would ideally by non-complementary to each other to prevent cross hybridisation with each other and should minimally cross-hybridise with the complementary sequences of all other sorting sequences. Minimally cross-hybridising sets of oligonucleotides that can be synthesised in a combinatorial process are disclosed in PCT/US95/12678. A series of sequencing templates identified by different primers linked to distinct sorting sequences can be used to generate Sanger ladders in the same reaction with the same labelled nucleotide terminators. The resultant Sanger ladders can then be sorted onto a hybridisation array comprising the sequences complementary to the sorting sequences so that each Sanger ladder identified by a particular primer can be sorted to a discrete location on the array.

What is claimed is:

1. A method for characterising nucleic acid, which method comprises either:

(a) contacting a plurality of nucleic acid templates with an array of adaptors, each adaptor in the array comprising a single-stranded portion of a common length and optionally a double-stranded primer, all possible base sequences of the single-stranded portion being represented in the array, the label on each primer being specific to the sequence of the single-stranded portion of that primer; and (b) introducing a base sequence of a common length into each nucleic acid template of a plurality of such templates, the base sequence being specific to that template, and contacting the nucleic acid templates with an array of primers each primer in the array comprising a single-stranded portion complementary to one of the base sequences introduced into the templates and optionally a double-stranded portion of a known sequence, all of the complementary sequences to the base sequences introduced into the templates being present in the array, the label on each primer being specific to the sequence of the single-stranded portion of that primer;

and then generating Sanger ladder nucleic acid fragments from the resulting nucleic acid templates in the same reaction mixture, at least one terminating base being present in the reaction zone, and for each nucleic acid fragment produced identifying the length of the fragment, the identity of the template from which the fragment is derived and the terminating base of the fragment, wherein prior to generating the fragments a labelled primer nucleotide or oligonucleotide is hybridised to each template, the label on each primer being specific to the template to which that primer hybridises to allow identification of the template.

2. A method according to claim 1, wherein prior to generating the Sanger ladder fragments, the nucleic acid templates are contacted with an array of adaptors, each adaptor in the array comprising a single-stranded portion of a common length and optionally a double-stranded primer portion, all possible base sequences of the single-stranded portion being represented in the array, the label on each primer being specific to the sequence of the single-stranded portion of the adaptor to which that primer is complementary.

3. A method according to claim 2, wherein the double-stranded primer portion of the adaptor comprises a known sequence.

4. A method according to claim 2, wherein the double-stranded primer portion of the adaptor comprises a sequence specific to its single-stranded portion, such that each Sanger ladder fragment produced will be terminated with a sequence specific to its template, to allow fragments from a specific template to be captured on solid phase by hybridization.

5. A method according to claim 1, which method further comprises introducing a base sequence of a common length into each nucleic acid template prior to generating the Sanger ladder fragments, the base sequence being specific to that template, and contacting the nucleic acid templates with an array of primers each primer in the array comprising a single-stranded portion complementary to one of the base sequences introduced into the templates and optionally a double-stranded portion of a known sequence, all of the complementary sequences to the base sequences introduced into the templates being present in the array, the label on each primer being specific to the sequence of the single-stranded portion of that primer.

6. A method according to claim 5, wherein the length of the single-stranded portion of each primer in the array is 2, 3, 4, 5 or 6 bases.

7. A method according to claim 1, wherein each primer has a label specific to the terminating base present in the reaction mixture.

8. A method according to claim 7, wherein each primer has one label, the label being specific to the template and the terminating base present in the reaction mixture.

9. A method according to claim 1, wherein a plurality of terminating bases are present in the reaction mixture, each terminating base comprising a label specific to that base.

10. A method according to claim 9, wherein 4 terminating bases are present in the reaction mixture.

11. A method according to claim 1, wherein the nucleic acid templates are generated by the action of an endonuclease on parent nucleic acid.

12. A method according to claim 11, wherein the endonuclease is a type IIs or type Ip endonuclease.

13. A method according to claim 1, wherein the nucleic acid templates are selectively amplified prior to generating the Sanger ladder fragments.

14. A method according to claim 1, wherein the Sanger ladder fragments are generated by employing a thermostable polymerase, and the step of generating the fragments is repeated as many times as desired by denaturing the fragments from the templates, allowing further primers to hybridize to the templates and extending the primers along the template to form further fragments, to linearly amplify the quantities of the fragments.

15. A method according to claim 1, wherein the identification of the length of the fragments and/or the identity of the templates and/or the identity of the terminating base is carried out by capillary electrophoresis mass spectrometry.

16. A method according to claim 5, wherein the labels on the primers and/or the labels on the terminating bases are mass labels.

17. A method according to claim 1, wherein all 4 terminating bases are present in a single reaction mixture, each terminating base having a label specific to that base, wherein the primers hybridized to the templates are not labeled, which method further comprises separating fragments generated from different templates according to a sequence of pre-determined length at a pre-determined position within the fragments.

18. A method according to claim 17, wherein the pre-determined position is adjacent the primer portion of the fragments.

19. A method according to claim 17, wherein the pre-determined length of the sequence is 1, 2, 3, 4, 5 or 6 bases.

20. A method for characterizing nucleic acid which comprises hybridizing an array of labeled primer oligonucleotides to a plurality of nucleic acid templates present in the same reaction mixture and then generating nucleic acid fragments by a Sanger ladder method from the labeled templates.

21. A method according to claim 2, wherein the length of the single-stranded portion of each adaptor in the array is 2, 3, 4, 5 or 6 bases.

* * * * *